United States Patent
Jiang et al.

(10) Patent No.: US 10,759,642 B2
(45) Date of Patent: Sep. 1, 2020

(54) CAP REMOVAL DEVICE AND THROMBELASTOGRAPHY DEVICE HAVING SAME

(71) Applicant: NEOTEK BIOSCIENCE CO., LTD., Suzhou, Jiangsu (CN)

(72) Inventors: Feng Jiang, Jiangsu (CN); Jian Xiao, Jiangsu (CN); Gong Liu, Jiangsu (CN); Aiqin Chen, Jiangsu (CN); Bangzhong Yu, Jiangsu (CN)

(73) Assignee: NEOTEK BIOSCIENCE CO., LTD., Suzhou, Jiangsu (CN)

( * ) Notice: Subject to any disclaimer, the term of this patent is extended or adjusted under 35 U.S.C. 154(b) by 0 days.

(21) Appl. No.: 16/097,556

(22) PCT Filed: May 2, 2017

(86) PCT No.: PCT/CN2017/082785
§ 371 (c)(1),
(2) Date: Oct. 29, 2018

(87) PCT Pub. No.: WO2017/186189
PCT Pub. Date: Nov. 2, 2017

(65) Prior Publication Data
US 2019/0210856 A1    Jul. 11, 2019

(30) Foreign Application Priority Data

Apr. 29, 2016   (CN) ........................... 2016 1 0278391
Apr. 29, 2016   (CN) ........................... 2016 1 0278393
(Continued)

(51) Int. Cl.
*B67B 3/28*      (2006.01)
*G01N 33/86*    (2006.01)
*G01N 33/49*    (2006.01)

(52) U.S. Cl.
CPC ........... *B67B 3/28* (2013.01); *G01N 33/4905* (2013.01); *G01N 33/86* (2013.01)

(58) Field of Classification Search
CPC ....... B67B 3/28; G01N 33/4905; G01N 33/86
See application file for complete search history.

(56) References Cited

U.S. PATENT DOCUMENTS 6,225,126 B1   5/2001   Cohen et al.
6,866,820 B1   3/2005   Otto et al.
(Continued)

FOREIGN PATENT DOCUMENTS

CN   103011040 A   4/2013
CN   103398922 A   11/2013
(Continued)

OTHER PUBLICATIONS

International Search Report issued for International Patent Application No. PCT/CN2017/082785, dated Jul. 24, 2017, 10 pages including English translation.
(Continued)

*Primary Examiner* — Krishnan S Menon
*Assistant Examiner* — Dwan A Gerido
(74) *Attorney, Agent, or Firm* — Hamre, Schumann, Mueller & Larson, P.C.

(57) ABSTRACT

A cap removal device and a thrombelastography device having same are disclosed. The cap removal device comprises a drive part (1), a connection shaft (2), and a cap removal member (3). The connection shaft (2) can move upward when driven by the drive part (1). The cap removal member (3) has an end (31) and the other end (32); the end (31) is pivotally connected to the connection shaft (2), so that when the connection shaft (2) moves upward when driven by the drive part (1), the cap removal member (3) rotates, due to the upward movement, around a pivot point (Continued)

(4) located between the end (31) and the other end (32) of the cap removal member (3), so that the other end (32) of the cap removal member (3) moves downward to contact a cap (5) to be removed, thereby removing the cap (5). The thrombelastography device has the cap removal device, and thus can achieve the automatic removal of the cap (5) and the automated control on the drive part (1), thereby improving the cap removal efficiency and the test efficiency, and saving time of manually removing the cap.

13 Claims, 6 Drawing Sheets

(30) Foreign Application Priority Data

| Apr. 29, 2016 | (CN) | ........................ 2016 1 0279824 |
| Apr. 29, 2016 | (CN) | .................... 2016 2 0380387 U |
| Apr. 29, 2016 | (CN) | .................... 2016 2 0380641 U |
| Apr. 29, 2016 | (CN) | .................... 2016 2 0383166 U |

(56) References Cited

U.S. PATENT DOCUMENTS

| 2010/0154520 A1 | 6/2010 | Schubert et al. |
| 2016/0091516 A1 | 3/2016 | Gorin et al. |

FOREIGN PATENT DOCUMENTS

| CN | 104062207 A | | 9/2014 |
| CN | 104181311 A | | 12/2014 |
| CN | 104458503 | * | 3/2015 |
| CN | 104614539 A | | 5/2015 |
| WO | 2010081876 | | 7/2010 |

OTHER PUBLICATIONS

Extended European Search Report issued for European Patent Application No. 17788841.9, dated Feb. 3, 2020, 6 pages.

* cited by examiner

CAP REMOVAL DEVICE AND THROMBELASTOGRAPHY DEVICE HAVING SAME

TECHNICAL FIELD

The present invention relates to the technical field of testing, and in particular, to a cap removal device and a thrombelastography device having the same.

BACKGROUND

A thrombelastography device is an apparatus which is configured to test blood coagulation data of blood in vitro, and monitor the blood coagulation process from entire dynamic processes, such as platelet aggregation, blood coagulation and fibrinolysis, thereby obtaining rates of blood coagulation and fibrinolysis, the strength of coagulation and the like. The rates of blood coagulation and fibrinolysis and the strength of coagulation can be used as a basis for clinical diagnosis of diseases, such as cardiovascular and cerebrovascular diseases.

In the existing thrombelastography device, a cap of a cup needs to be buckled with a cup body containing liquid (e.g., blood) in blood testing. At the end of testing, since the blood may be adhered to the cap of the cup, it is necessary to replace the cap of the used cup in order to improve the accuracy in next testing.

SUMMARY

In view of this, embodiments of the present invention provide a cap removal device and a thrombelastography device having the same.

According to an aspect of the present invention, the present invention provides a cap removal device which comprises a drive part, a connection shaft, and a cap removal member, wherein the connection shaft can move upward when driven by the drive part; the cap removal member has an end and the other end; the end is pivotally connected to the connection shaft, so that when the connection shaft moves upward when driven by the drive part, the cap removal member rotates, due to the upward movement, around a pivot point located between the end and the other end of the cap removal member, so that the other end of the cap removal member moves downward to contact a cap to be removed, thereby removing the cap.

According to another aspect of the present invention, the present invention provides a thrombelastography device, comprising a support, a rotary shaft and the cap removal device, wherein the support is connected to one end of the rotary shaft to support the rotary shaft, such that the rotary shaft is able to rotate, wherein the rotary shaft is able to be sleeved with the cap to be removed the cap removal device comprises a drive part, a connection shaft, and a cap removal member, wherein the connection shaft can move upward when driven by the drive part;

the cap removal member has an end and the other end; the end is pivotally connected to the connection shaft, so that when the connection shaft moves upward when driven by the drive part, the cap removal member rotates, due to the upward movement, around a pivot point located between the end and the other end of the cap removal member, so that the other end of the cap removal member moves downward to contact a cap to be removed, thereby removing the cap;

the cap removal member is pivotally connected to the support at the pivot point; and the other end of the cap removal member is provided with an opening that allows the rotary shaft to pass through in a manner substantially perpendicular to the other end, such that the other end sleeves the rotary shaft and is located above the cap.

The cap removal device and/or the thrombelastography device provided by various embodiments of the present invention can realize the automatic removal of a cap of a container for containing measured blood, without manual cap removal, thereby improving the testing efficiency and avoiding measurement errors caused by repeated use of the cap to which the measured blood is blotted in the next measurement.

The above summary is only for an illustrative purpose and is not intended to be limited in any way. Except for the aspects, embodiments and features as described above, further aspects, embodiments, and features of the present invention will be readily apparent from the appended drawings and the following detailed description.

BRIEF DESCRIPTION OF THE DRAWINGS

In the drawings, unless otherwise specified, the same reference numerals used throughout the drawings refer to the same or similar components and elements. The drawings are not necessarily to scale. It is should be understood that these drawings are merely illustrative of some embodiments of the present invention and are not to be construed as limiting the scope of the present invention.

DETAILED DESCRIPTION

Figure 1:
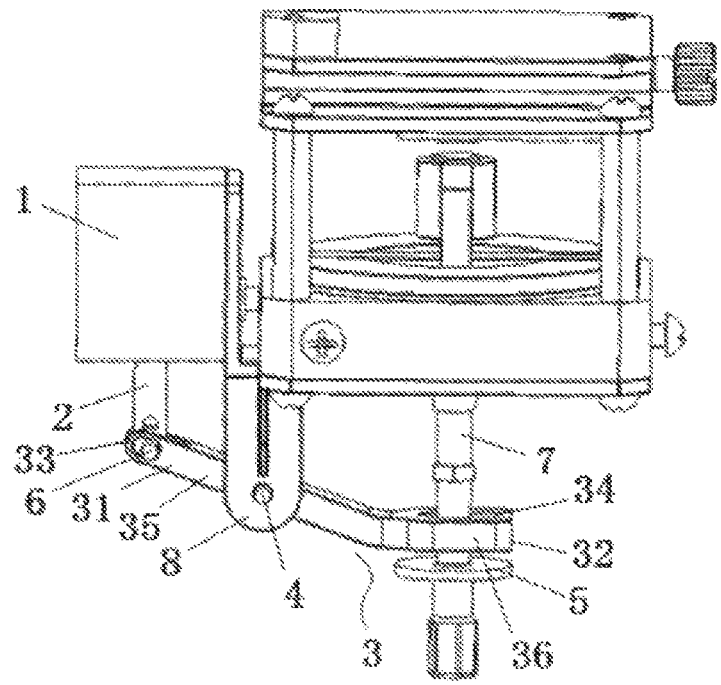
FIG. 1 is a schematic diagram of a cap removal device and a thrombelastography device provided by an embodiment of the present invention.

In the following, only certain exemplary embodiments are briefly described. As those skilled in the art will recognize, the described embodiments may be modified in various different ways, without departing from the spirit or scope of the present invention. Therefore, the drawings and description are to be regarded as exemplary, rather than restrictive.

In the description of the present invention, it should be understood that, the terms "center", "longitudinal", "transverse", "length", "up", "down", "front", "rear", "left", "right", "vertical", "horizontal", "top", "bottom", "inner", "outer", "clockwise", "counterclockwise" and the like, which denote orientations or positional relationship, are based on the orientations or positional relationships shown in the drawings, for the purposes of describing the present invention and simplifying the description, do not indicate or imply that the device or component referred to necessarily has a specific orientation or is constructed and operated according to a specific orientation, and are therefore not to be construed as limiting the present invention. Moreover, the terms "first" and "second" are used for descriptive purposes only and are not to be construed as indicating or implying a relative importance or implicitly indicating the number of technical features indicated. Thus, features defining "first" or "second" may include one or more of the described features, either explicitly or implicitly. In the description of the present invention, the meaning of "a plurality of" is two or more, unless specifically defined otherwise.

As shown in FIG. 1, an embodiment of the present invention provides a cap removal device. The cap removal device comprises a drive part 1, a connection shaft 2, and a cap removal member 3, wherein the connection shaft 2 can move upward when driven by the drive part 1;

a first end 31 of the cap removal member 3 is pivotally connected to the connection shaft 2, so that when the connection shaft 2 moves upward when driven by the drive part 1, the cap removal member 3 rotates, due to the pivotal connection between the connection shaft 2 and the first end 31, around a pivot point 4 located between the first end 31 and a second end 32 of the cap removal member 3 (in a clockwise direction as viewed from the angle in FIG. 1), so that the second end 32 of the cap removal member 3 moves downward to contact a cap 5 to be removed, thereby removing the cap 5 under the downward force applied by the second end 32.

In an embodiment of the present invention, the connection shaft 2 can further move downward under a driving force of the drive part 1, such that the cap removal member 3 after the completion of the cap removal operation can be reset to prepare for the next cap removal operation. Here, the case where the connection shaft and the cap removal member are reset "under the driving force of the drive part" means that the drive part generates a downward driving force to the connection shaft, or the drive part reduces or eliminates an upward driving force applied to the connection shaft, such that the connection shaft and the cap removal member move downward under their own gravity to be reset.

In an embodiment, the travel of the connection shaft that can move upward and downward under the driving force of the drive part is approximately 4 mm.

Specifically, when the connection shaft 2 moves downward under the driving force of the drive part 1, the pivotal connection between the connection shaft 2 and the first end 31 rotates the cap removal member 3 around the pivot point 4 (in a counterclockwise as viewed from the angle in FIG. 1), such that the second end 32 of the cap removal member 3 moves upward, the connection shaft 2 moves downward to its initial position, and the second end 32 of the cap removal member 3 moves upward to its initial position to complete resetting.

As shown in FIG. 1, in order to facilitate flexible movement of the cap removal member 3, the first end 31 of the cap removal member 3 is provided with a through hole 33. The first end 31 passes through the through hole 33, and is connected to a pivot shaft 6 of the connection shaft 2 and pivotally connected to the connection shaft 2, such that the cap removal member 3 can rotate under the driving of the connection shaft 2.

In an example, the drive part 1 drives the connection shaft 2 to move in a linear direction parallel to the axis of the connection shaft 2. In order to prevent the occurrence of the problem that the movement failure occurs when the cap removal member 3 rotates relative to the connection shaft 2, the dimension of the through hole 33 in the length direction of the cap removal member 3 may be larger than the diameter of the pivot shaft 6, such that the pivot shaft 6 can slide in the through hole 33 when the connection shaft 2 moves upward and downward to drive the cap removal member 3 to rotate around the pivot point 4, thereby ensuring a linear movement of the connection shaft 2 along its own axis direction and the circumferential movement of the cap removal member 3 along the fixed pivot point 4. In another embodiment, the dimension of the through hole 33 is exactly matched with the diameter of the pivot shaft 6, so that the pivot shaft 6 cannot translate within the through hole 33. However, the position of the pivot point 4 relative to the cap removal member 3 is fixed. Specifically, the pivot shaft for pivotally connecting the cap removal member 3 at the pivot point 4 and the through hole, which is used for accommodating the pivot shaft, in the cap removal member 3 are arranged in such a manner: the dimension of the through hole in the length direction of the cap removal member 3 is larger than the diameter of the pivot shaft, such that when the connection shaft 2 moves upward and downward to drive the cap removal member 3 to rotate around the pivot point 4, the pivot shaft can slide within the through hole, thereby ensuring that the connection shaft moves linearly along its own axis.

In an embodiment of the present invention, the cap removal device may further comprise a control unit which is configured to, in response to a cap removal request, control the drive part 1 to drive the connection shaft 2 to move upward. In an example, the cap removal request may be a signal indicating that previous measurement has been completed, which is detected by the control unit itself or detected by other components and sent to the control unit, or may be a cap removal request which is sent to the control unit or other components by a user through an input component. The control unit sends a control signal to the drive part 1 after receiving the cap removal request, and controls the drive part to operate, so as to drive the connection shaft 2 to move upward to an appropriate position where the cap can be removed, for example, the maximum travel position of the connection shaft. In this way, automatic control of the drive part 1 is achieved, automatic execution of the cap removal operation of the cap removal member 3 can be driven, the operation efficiency is improved, and therefore the cap 15 can be removed more conveniently.

In an example, after the control unit sends a control signal to cause the drive part to drive the connection shaft such that the cap removal member knocks off the cap for a predetermined time, for example, about 2 seconds after sending the control signal, the control unit may transmit to another control signal to the drive part, such that drive part applies a downward driving force to the connection shaft or reduces or eliminates the applied upward driving force, thereby resetting the connection shaft and the cap removal member.

In an example, the control unit may send a control signal to the drive part, such that the drive part drives the cap removal member to execute the cap removal operation for a plurality of times within a short time, thereby ensuring that the cap is knocked off.

In an embodiment of the present invention, as shown in FIG. 1, the cap removal member 3 comprises a first part 35 and a second part 36 which are fixedly connected, wherein the first part 35 comprises a first end 31, and the second part 36 comprises a second end 32. The first part 35 and the second part 36 are arranged to form a certain inclination angle.

In an example, the first part 35 is arranged to form an inclination angle with the top surface of the cap, and the second part 36 is arranged to be substantially parallel to the top surface of the cap, such that when the first part 35 rotates around the pivot point 4, the second end of the second part 36 can ensure the maximum contact with the top surface of the cap 5 and ensure that the cap 5 can be knocked off.

It needs to be noted that the included angle between the first part 35 and the second part 36 may be any appropriate angle, as long as the second end 32 of the cap removal member 3 is substantially parallel to the top surface of the cap 5.

In an embodiment of the present invention, the pivot point 4 is located on the first part 35, as shown in FIG. 1.

In an example, the drive part 1 is an electromagnet, and at least a portion of the connection shaft 2 is composed of a material that can be attracted (or otherwise magnetically repelled) by the magnetic force of the magnet. In this example, the control unit controls, in response to the cap removal request, the supply of an appropriate current to the electromagnet, such that the electromagnet generates a magnetic force, and further the connection shaft moves upward under the attraction of the magnetic force. When a reset is required, the control unit may control to cut off or change the current supplied to the electromagnet, so that the magnetic force disappears or decreases, and further the connection shaft moves downward due to the gravity.

In another example, the drive member part is an electromagnet and at least a portion of the connection shaft 2 is a magnet material. In this example, the control unit controls, in response to the cap removal request, the supply of a current in an appropriate direction to the electromagnet, such that the electromagnet generates a magnetic force that is attracted to the connection shaft, and further the connection shaft moves upward under the attraction of the magnetic force. When a reset is required, the control unit may control to or reduce the current supplied to the electromagnet or change its current direction, such that the magnetic force disappears or decreases or becomes a magnetic force repelling the connection shaft, and further the connection shaft moves downward due to the gravity and/or repulsive force.

It will be appreciated that, in addition to the example of the electromagnet described above, the "drive part" herein may be any other component capable of driving the connection shaft to move, such as a motor, a lifting mechanism, or the like.

Figure 13:
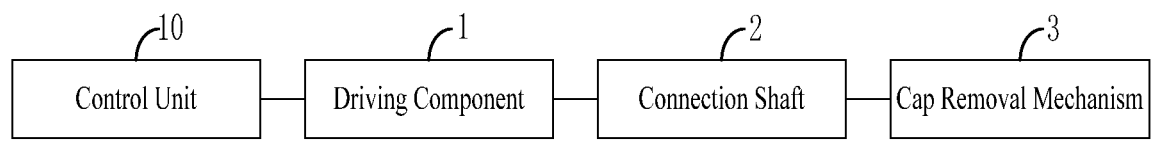
FIG. 13 is a schematic block diagram of a cap removal device provided by an embodiment of the present invention.

FIG. 13 is a schematic block diagram of a cap removal device provided by an embodiment of the present invention. As shown in FIG. 13, the cap removal device comprises a control unit 10, a drive part 1, a connection shaft 2 and a cap removal member 3. The drive part 1 drives the connection shaft 2 to move upward under the control of the control unit 10, thereby driving the cap removal member 3 whose one end is pivotally connected to the connection shaft to rotate around a fixed pivot point, and further allowing the other end of the cap removal member 3 to move downward to knock off the cap.

Although the cap removal device is shown and described herein for use with a thrombelastography device, those skilled in the art will recognize that the cap removal device of various embodiments of the present invention may be used with other instrument devices as well.

In an embodiment of the thrombelastography device of the present invention, as shown in FIG. 1, the cap 5 sleeves a rotary shaft 7, the second end 32 is provided with an opening 34, and the rotary shaft 7 passes through the opening 34 in a manner substantially perpendicular to the second end 32, such that the second end 32 sleeves the rotary shaft 7, and the cap 5 is located below the opening 34 on the rotary shaft 7. In an example, a hole is formed in the center of the cap 5 and allows the rotary shaft 7 to pass through, wherein the diameter of the hole is slightly smaller than the diameter of the rotary shaft 7 in a natural state. In addition, the cap 5 is made of a material having appropriate flexibility, so that the cap can be sleeved and pressed against the rotary shaft 7, and can be removed from the rotary shaft 7 while being subjected to an appropriate external force.

It should be noted that the width of the opening 34 is larger than the diameter of the rotary shaft 7, that is, the opening 34 sleeves the rotary shaft 7 and does not contact the rotary shaft 7 when moving or being stationary, thereby avoiding the interference to the rotational movement of the rotary shaft 7 when the opening 34 is in contact with the rotary shaft 7 in case that the rotary shaft 7 rotates. Meanwhile, the width of the opening 34 should be not larger than the diameter of the cap 5, i.e., when the second end 32 of the cap removal member 3 moves downward, the opening of the second end 32 can be ensured to come into contact with the cap 5, thereby removing the cap 5. In an example, the size of the opening 34 is adjustable.

In an example, in order to ensure that the cap 5 can be knocked off completely, the shape of the lower end surface of the second end 32 of the cap removal member 3 may be set to be substantially consistent with the shape of the cap 5, thereby maximizing the contact area between the second end 32 and the cap 5, so that the cap 5 can be removed from the rotary shaft 7 more easily.

In an embodiment of the present invention, as shown in FIG. 1, the rotary shaft 7 is supported by the support 8. The drive part 1 is fixed to a support 8, and the cap removal member 3 is pivotally connected to the support 8 at the pivot point 4. In an example, the cap removal member 3 is connected to the support 8 through a connection member. The connection member is fixedly connected to the support 8, and the cap removal member 3 is pivotally connected to the connection member at the pivot point 4.

As shown in FIG. 1, the drive part 1 is fixedly connected to one side of the support 8, and ensures that the drive part 1 can drive the connection shaft 2 to move upward and downward relative to the support 8 in a vertical direction. The pivot point 4 of the cap removal member 3 which is pivotally connected to the rotary shaft 2 is pivotally connected to the lower part (or the connection member) of the support 8. The rotary shaft 7 is supported on the support 8 in a vertically downward manner. The opening 34 of the second end 32 of the cap removal member 3 sleeves a position, close to the tail end, of the rotary shaft 7. The cap 5 sleeves the rotary shaft 7, and is located below the opening 34.

When the cap removal device of the present invention operates, the control unit is configured to, in response to a cap removal request, control the drive part 1 to drive the connection shaft 2 to move upward. When the rotary shaft 2 moves upward, the first end 31 of the cap removal member 3, which is connected to the connection shaft 2, is pulled upward, thereby driving the cap removal member 3 to rotate around the pivot point 4. When the first end 31 of the cap removal member 3 moves upward, the second end 32 moves downward till contacting the cap 5. When the second end 32 continues to move downward, the lower end surface of the second end 32 is in contact with the top surface of the cap 5 and presses the cap 5, such that the cap 5 is removed from the rotary shaft 7, thereby completing the cap removal operation of the cap removal member 3.

The connection shaft 2 may be driven downward by the control unit before the next cap removal operation is required. When the connection shaft 2 moves downward, the first end 31 of the cap removal member 3, which is connected to the connection shaft 2, moves downward together to drive the cap removal member 3 to rotate around the pivot point 4. When the first end 31 of the cap removal member 3 moves downward, the second end 32 moves upward substantially along the rotary shaft 7 to an initial position, thereby completing a resetting operation of the cap removal member 3.

An embodiment of the present invention provides a thrombelastography device. As shown in FIG. 1, the thrombelastography device comprises a support 8, a rotary shaft 7 and the cap removal device, wherein the support 8 is connected to one end of the rotary shaft 7 to support the rotary shaft 7, such that the rotary shaft 7 is able to rotate under an external driving force;

the cap removal member 3 is pivotally connected to the support 8 at the pivot point 4;

a second end 32 of the cap removal member 3 is provided with an opening 34 that allows the rotary shaft 7 to pass through in a manner substantially perpendicular to the second end 32, such that the second end 32 sleeve the rotary shaft 7; and the cap 5 sleeves the rotary shaft 7 and is located below the opening 34.

Figure 2:
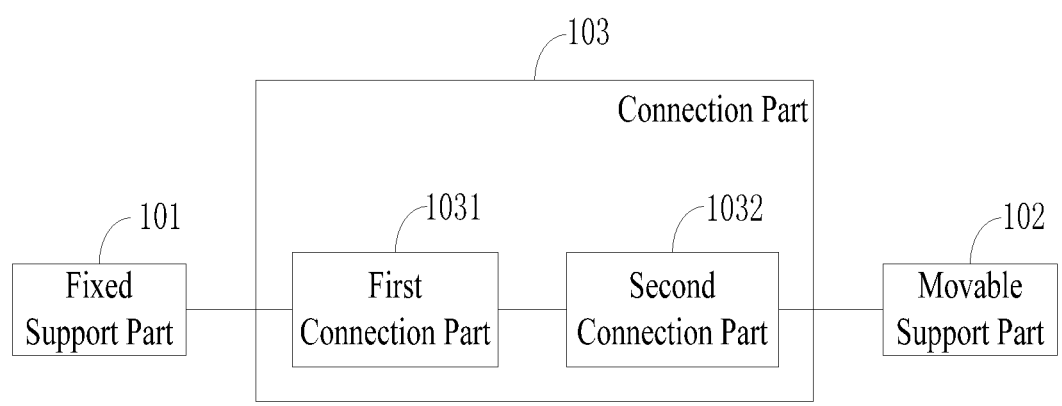
FIG. 2 is a schematic diagram of a support provided by an embodiment of the present invention.

In an embodiment of the present invention, as shown in FIG. 2, the support comprises a fixed support part 101, a movable support part 102, a first connection part 1031 and a second connection part 1032, wherein the first connection part 1031 is fixedly connected to the fixed support part 101, and the second connection part 1032 is fixedly connected to the movable support part 102;

the first connection part 1031 and the second connection part 1032 are connected together in a form of point contact, such that the second connection part 1032 is able to rotate relative to the first connection part 1031;

the movable support part 102 is fixedly connected to an external supported object; and the movable support part 102 rotates relative to the fixed support part 101 under the driving force of the supported object by means of the point contact between the first connection part 1031 and the second connection part 1032.

In an example as shown in FIG. 2, the fixed support part 101 supports the movable support part and the supported object by means of the connection part, the first connection part 1031 and the second connection part 1032 in the connection part are connected together in a form of point contact, and the supported object which is in stress drives the movable support part 102 to rotate around the contact point between the first connection part 1031 and the second connection part 1032. Since the first connection part 1031 and the second connection part 1032 are connected together in a form of point contact, when the movable support part 102 and the fixed support part 101 rotate relative to each other, only one contact point generates a frictional force to impede the rotation of the movable support part 102. Therefore, the frictional force generated on the support may be reduced, and further the rotational resistance encountered when the supported object rotates is reduced.

In the embodiment provided by the present invention, the point connection may resides in that: two contact components are not in full contact and the contact area is less than a predetermined value. For example, when the first connection part 1031 and the second fixed connection part 1032 are connected together in a form of point contact, the contact area is less than 1 square millimeter.

Figure 3:
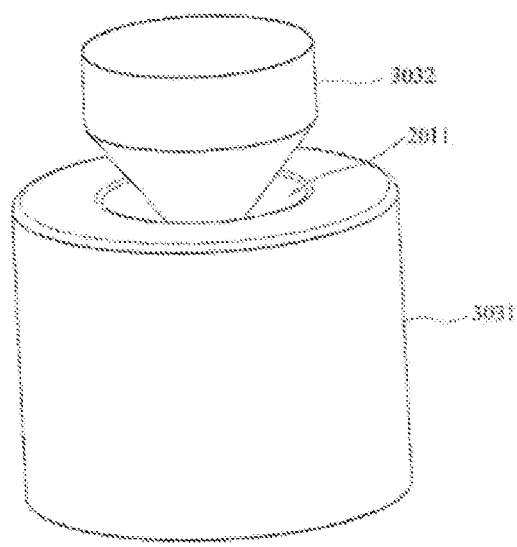
FIG. 3 is a schematic diagram of a connection part provided by an embodiment of the present invention.

In an example shown in FIG. 3, the first connection part 1031 comprises a jewel bearing 3031, and the second connection part 1032 comprises a top cone 3032;

or the first connection part 1031 comprises a top cone 3032, and the second connection part 1032 comprises a jewel bearing 3031; wherein the jewel bearing 3031 is provided with a tapered groove 2011; the top cone 3032 may be of a tapered structure, and the tip of the top cone 3032 is located in the tapered groove 2011 in the jewel bearing 3031; the top cone 3032 is engaged to the jewel bearing 3031 in a form of point contact.

As shown in FIG. 3, the jewel bearing 3031 is of a cake structure. The tapered groove 2011 is formed in a plane of the jewel bearing 3031. The top cone 3032 may be of a tapered structure. The tip of the top cone 3032 is located in the groove 2011, and only the tip of the top cone 3032 is in contact with the bottom of the groove 2011, such that the jewel bearing 3031 is connected to the top cone 3032 in a form of point contact. For example, when the tip of the top cone 3032 has an area of 0.8 square millimeter, the top cone is connected to the tapered groove 2011 of the jewel bearing 3031 in a form of point contact by means of this tip having the area of 0.8 square millimeter.

In an embodiment of the present invention, the first connection part in the connection part may be a jewel bearing or a top cone. When the first connection part is the jewel bearing, the second connection part is a top cone. When the first connection part is the top cone, the second connection part is the jewel bearing. The structure of the support will be described below in the following cases in which the first connection part is the jewel bearing and the first connection part is the top cone, respectively.

Figure 4:
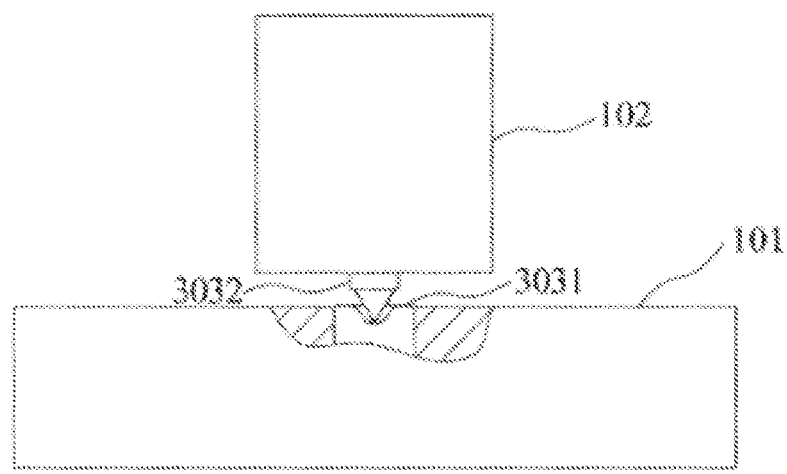
FIG. 4 is a support schematic diagram in which a jewel bearing is fixedly connected to the fixed support part as provided by an embodiment of the present invention.

In an embodiment of the present invention, as shown in FIG. 4, the jewel bearing 3031 which serves as the first connection part is fixedly connected to the fixed support part 101, the top cone 3032 which serves as the second connection part is fixedly connected to the movable support part 102, and the tip of the top cone 3032 is located in a groove of the jewel bearing 3031 and is in point contact with the bottom of the groove of the jewel bearing 3031. The fixed support part 101 supports, by means of the jewel bearing 3031, the top cone 3032 and the movable support part 102 which are fixedly connected.

Figure 5:
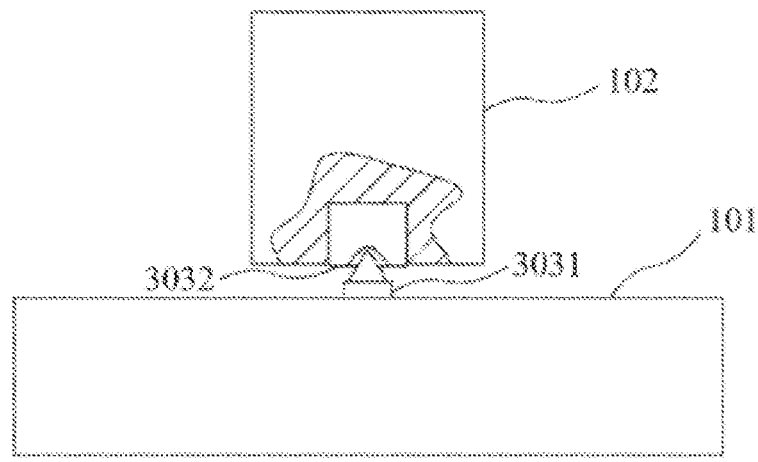
FIG. 5 is a support schematic diagram in which the jewel bearing is fixedly connected to the movable support part as provided by an embodiment of the present invention.

In another embodiment of the present invention, as shown in FIG. 5, the top cone 3031 which serves as the first connection part is fixedly connected to the fixed support part 101, the jewel bearing 3032 which serves as the second connection part is fixedly connected to the movable support part 102, and the tip of the top cone 3031 is in point contact with the bottom of the jewel bearing 3032. The fixed support part 101 supports, by means of the top cone 3031, the jewel bearing 3032 and the movable support part 102 which are fixedly connected.

In an embodiment of the present invention, the support further comprises at least a pair of magnets;

for each pair of magnets, the first magnet is fixed to one side, close to the movable support part, on the fixed support part, and the second magnet is fixed to one side, close to the fixed support part, on the movable support part; and the first magnet and the second magnet are stacked in parallel, and two surfaces that are close each other are the like magnetic poles.

The support provided by the embodiment of the present invention will be further described below by taking the support which comprises two pairs of magnets as an example.

Figure 6:
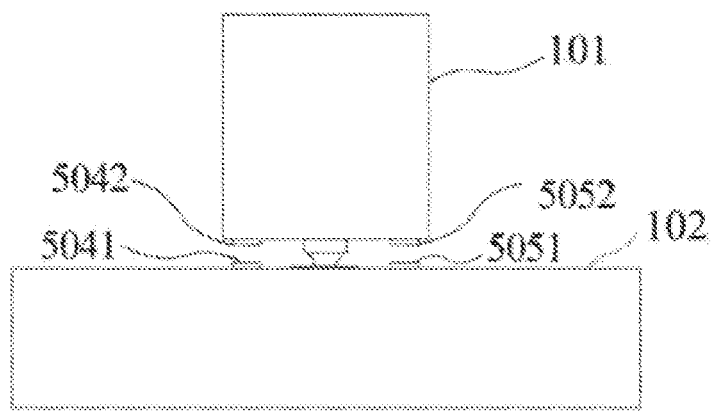
FIG. 6 is a support schematic diagram comprising magnets as provided by an embodiment of the present invention.

In an embodiment of the present invention, as shown in FIG. 6, the support comprises two pairs of magnets. The first pair of magnets includes a magnet 5041 and a magnet 5042. The second pair of magnets includes a magnet 5051 and a magnet 5052. The magnet 5041 and the magnet 5051 are fixed to the fixed support part 101, and the magnet 5042 and the magnet 5052 are fixed to the movable support part 102. The magnet 5041 and the magnet 5042 in the first pair of magnets are stacked in parallel. The surfaces, which are close to each other, of the magnet 5041 and the magnet 5042 have magnetic poles which have the same polarity, for example, the N pole of the magnet 5041 is directed to the movable support part 102, and the N pole of the magnet 5042 is directed to the fixed support part 101; the magnet 5051 and the magnet 5052 in the second pair of magnets are stacked in parallel; the surfaces, which are close to each other, of the magnet 5051 and the magnet 5052 have magnetic poles which have the same polarity, for example, the S pole of the magnet 5051 is directed to the movable support part 102, and the S pole of the magnet 5052 is directed to the fixed support part 101.

In an embodiment of the present invention, the thrombelastography device further comprises a measurement device which is used for measuring a rotation angle of the rotary shaft, and forming a thrombelastogram corresponding to measured blood according to the rotation angle of the rotary shaft.

Figure 7:
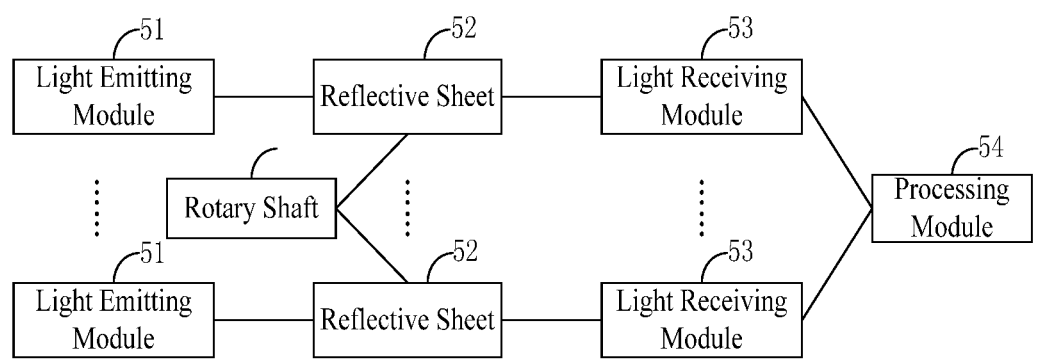
FIG. 7 is a schematic diagram of a thrombelastography device comprising a measurement device as provided by an embodiment of the present invention.

In an embodiment of the present invention, as shown FIG. 7, the measurement device comprises at least one reflective sheet 51, at least one light emitting module 52, at least one light receiving module 53 and a processing module 54, wherein the rotary shaft 7 is fixedly connected to the at least one reflective sheet 51 and drives the at least one reflective sheet 51 to rotate under an external driving force;

each of the light emitting modules 52 is used for emitting light to the corresponding reflective sheet 51 in a fixed direction;

each of the reflective sheets 51 is used for receiving light emitted y the corresponding light emitting module 52 and reflecting the received light;

each of the light receiving modules 53 is used for receiving light reflected by the corresponding reflective sheet 51 in a fixed direction, converting the received light into a corresponding electrical signal according to the intensity of the light, and transmitting the electrical signal to the processing module 54; and the processing module 54 is used for processing the electrical signal converted by the at least one light receiving module 53 to determine the rotation angle of the rotary shaft 7.

In the thrombelastography device provided by the embodiment of the present invention, the reflective sheet reflects the light emitted by the light emitting module to the light receiving module. When the reflective sheet rotates under the driving of the rotary shaft, since the light emitting module emits light in a fixed direction, the amount of light received by the reflective sheet changes, and at the same time, the optical path of light reflected by the reflective sheet changes due to the rotation of the reflective sheet, resulting in a change in the intensity of light received by the light receiving module that receives the light in the fixed direction. The light receiving module converts the received light into a corresponding electrical signal according to the intensity of the light. The processing module determines the rotation angle of the rotary shaft according to the electrical signal. In this case, the light is taken as a signal for detecting the rotation angle of the rotary shaft. Since the intensity of the light does not change as external factors such as temperature change, the accuracy of detecting the rotation angle of the rotary shaft can be improved by detecting the rotation angle of the rotary shaft through light.

Figure 8:
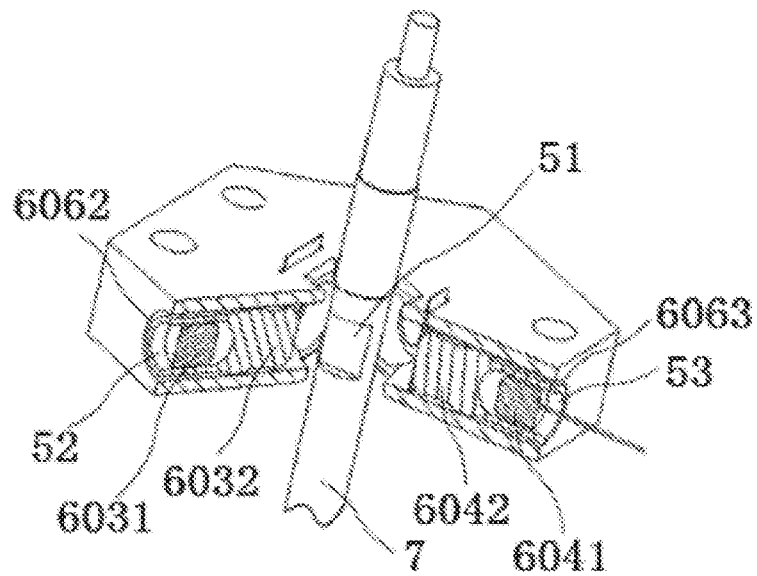
FIG. 8 is a schematic diagram of a thrombelastography device comprising a light emitting diode and a photocell as provided by an embodiment of the present invention.

In an embodiment of the present invention, as shown in FIG. 8, the light emitting module 52 comprises a light emitting diode 6031 and a light guide column 6032, wherein the light emitting diode 6031 emits light to the reflective sheet 51 through the light guide column 6032;

and/or the light receiving module 53 comprises a photocell 6041 and a light guide column 6042, wherein the photocell 6041 receives light reflected by the reflective sheet 51 through the light guide column 6042.

In the embodiment of the present invention, since the inner surface of a second through hole 6062 is a machined surface which has a certain roughness, if the light emitting diode 6031 directly emits light to the reflective sheet 51, the light emitted by the light emitting diode 6031 will be diffusely reflected within the second through hole 6062, resulting in loss of light energy on the one hand, and difficulty in control over the direction and amount of light outgoing from the second through hole 6062 on the other hand. The light emitted from the light emitting diode 6031 is directed to the reflective sheet 51 through the light guide column 6032. The light emitted from the light emitting diode 6031 is conducted inside the light guide column 6032, and may not be diffusely reflected, thereby improving the utilization rate of the light energy and ensuring that the light emitted from the second through hole 6062 has a specific direction and a specific amount, and further ensuring the accuracy of detecting the rotation angle of the rotary shaft 7.

In an embodiment of the present invention, each of the light receiving modules comprises a photocell and a light guide column which are fixed in a third through hole respectively, wherein the light guide column is located close to one of the reflective sheets. The light guide column receives the light reflected by the corresponding reflective sheet in a fixed direction, and transmits the received light to the photocell. The photocell converts the received light into a corresponding electrical signal according to the intensity of the light.

In an embodiment of the present invention, since the third through hole 6063 is formed by machining, the inner surface of the third through hole 6063 has a certain roughness. If the light reflected by the reflective sheet 51 directly enters the third through hole 6063 and reaches the photocell 6041, the light will be diffusely reflected on the inner wall of the third through hole 6063, resulting in the loss of light energy. The energy of the light finally reaching the photocell 6041 is less than the energy of the light entering the third through hole 6063, resulting in a relatively large error in the finally detected rotation angle of the rotary shaft 7. The light reflected by the reflective sheet 51 is received by the light guide column 6042, and the light is transmitted inside the light guide column 6042 and is not diffusely reflected during the transmission, thereby ensuring that the energy of the light received by the photocell 6041 is equal to the energy of light reflected by the reflective sheet 51 to the light guide column 6042, and further ensuring the accuracy of detecting the rotation angle of the rotary shaft 7.

In an embodiment of the present invention, the thrombelastography device further includes at least one light blocking sheet, the number of the light blocking sheets being equal to the number of the light guide columns, and each of the light blocking sheets corresponding to one of the light guide columns. Each light blocking sheet is provided with a light passing hole having a fixed shape and a fixed size. The light blocking sheet is arranged between the reflective sheet and the light guide column, so that the light reflected by the reflective sheet can only be emitted to the light guide column through the light passing hole in the light blocking sheet.

Figure 9:
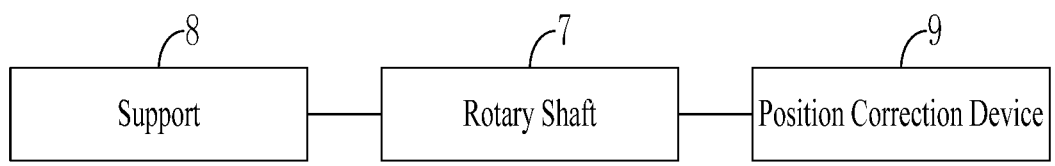
FIGS. 9-12 are schematic diagrams of a thrombelastography device comprising a correction device as provided by an embodiment of the present invention.

In an embodiment of the present invention, as shown in FIG. 9, the thrombelastography device further comprises a position correction device 9, wherein the other end of the rotary shaft 7 is placed in measured blood, and the rotary shaft 7 is able to rotate under the driving force of the measured blood; and the position correction device 9 is connected to the rotary shaft 7 and is used for generating, when the rotary shaft 7 rotates away from a balanced position, an acting force that rotates the rotary shaft 7 back to the balanced position.

The present invention provides a thrombelastography device, wherein the rotary shaft is able to rotate under the support of the support, and the position correction device is connected to the rotary shaft. When the rotary shaft rotates away from a balanced position under the driving force of the measured blood, the position correction device is caused to generate an acting force for rotating the rotary shaft towards the balanced position. In this way, when the driving effect of the measured blood on the rotary shaft is removed, if the position where the rotary shaft is located is not the balanced position, the rotary shaft automatically returns to the balanced position under the acting force of the position correction device, and thus does not need to be calibrated by manual adjustment. Therefore, the time of calibrating the rotary shaft is saved, and the efficiency in blood coagulation measurement is improved.

Figure 10:
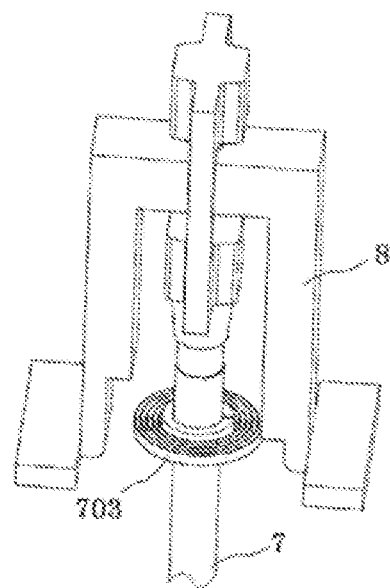

As shown in FIG. 10, the position correction device may comprise at least one hair spring 703, wherein an inner ring of the hair spring 703 is fixedly connected to an outer circumferential surface of the rotary shaft 7, and an outer ring of the hair spring is fixedly connected to the support 8. When the rotary shaft 7 is in the balanced position, the hair spring 703 is in a free state, and does not exert an acting force on the rotary shaft 7. When the rotary shaft 7 rotates under the driving force of the measured blood, the hair spring 703 rotates inward to deform or rotates outward to deform. The hair spring 703 restores an elastic force after being deformed. The function of restoring the elastic force is to restore the rotary shaft 7 to the balanced position, such that the hair spring 703 restores to the free state. When the driving force of the measured blood on the rotary shaft 7 is removed, if the position where the rotary shaft 7 is not the balanced position, the rotary shaft 7 rotates towards the balanced position as the hair spring 703 restores the elastic force, and finally the rotary shaft 7 restores to the balanced position.

In an embodiment of the present invention, when the position correction device 9 comprises two or more hair springs 703, the spiral direction of at least one of the hair springs 703 from the inner ring to the outer ring is different from the spiral direction of the other hair spring 703 from the inner ring to the outer ring.

Figure 11:
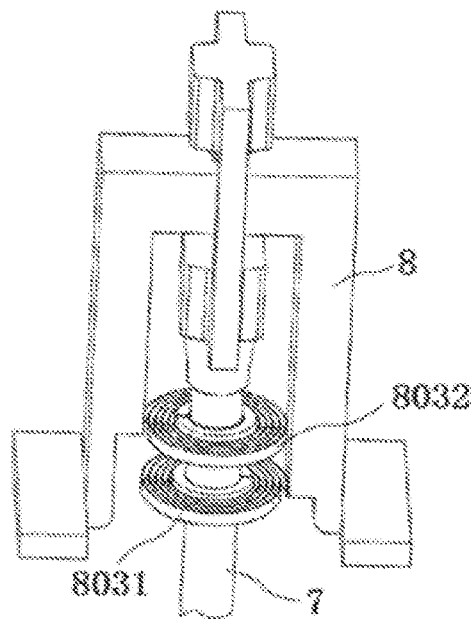

As shown in FIG. 11, the position correction device comprises a hair spring 8031 and a hair spring 8032, wherein inner rings of the hair spring 8031 and the hair spring 8032 are fixed to the rotary shaft 7 respectively, and outer rings of the hair spring 8031 and the hair spring 8032 are fixed to the support 8 respectively. As viewed from an observation position shown in FIG. 3, the spiral direction of the hair spring 8031 from the inner ring to the outer ring is clockwise, and the spiral direction of the hair spring 8032 from the inner ring to the outer ring is counterclockwise. When the rotary shaft 7 rotates counterclockwise, the hair spring 8031 is screwed, and when the rotary shaft 7 rotates clockwise, the hair spring 8032 is screwed.

Since the hair spring outputs a stable acting force when it is screwed than the acting force output when it is unscrewed, the hair spring is set to a different spiral direction. When the rotary shaft rotates in different directions, there is always a corresponding hair spring that is screwed to provide an acting force for the rotary shaft to restore to the balanced position. By means of such a structure, on the one hand, the rotary shaft rotates more stably, and on the other hand, the plastic deformation caused by excessive unscrewing of the hair spring can be avoided.

In an embodiment of the present invention, the position correction device further comprises at least one zero setting module, wherein each zero setting module corresponds to one hair spring. One end of each zero setting module is fixedly connected to the support, and the other end of the zero setting module is fixedly connected to different positions on the outer ring of the corresponding hair spring in an adjustable manner, so as to adjust the balanced position.

Figure 12:
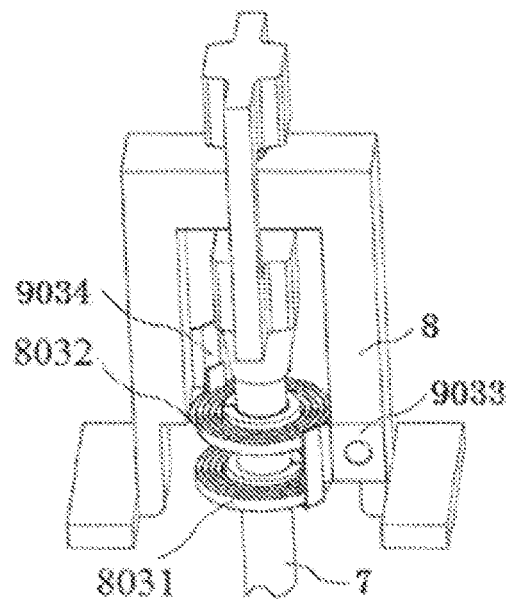

As shown in FIG. 12, the position correction device comprises a hair spring 8031, a hair spring 8032, a zero setting device 9033, and a zero setting device 9034, wherein the hair spring 8031 corresponds to the zero setting device 9033, and the hair spring 8032 corresponds to the zero setting device 9034. One end of the zero setting device 9033 is fixedly connected to the support 8, and the other end of the zero setting device 9033 is fixed to the outer ring of the hair spring 8031 by a U-shaped structure. A position, which is fixed to the U-shaped structure, on the outer ring of the hair spring 8031 is adjustable. One end of the zero setting device 9034 is fixedly connected to the support 8, and the other end of the zero setting device is fixed to the outer ring of the hair spring 8032 by a U-shaped structure. A position, which is fixed to the U-shaped structure, on the outer ring of the hair spring 8032 is adjustable. The inner rings of the hair spring 8031 and the hair spring 8032 are fixed to the outer circumferential surface of the rotary shaft 7.

By adjusting the position of the U-shaped structure on the zero setting device 9033, which is fixed on the outer ring of the hair spring 8031, as well as the position of the U-shaped structure on the zero setting device 9034, which is fixed on the outer ring of the hair spring 8032, the acting force applied by the two hair springs on the rotary shaft 7 when the rotary shaft 7 is not subjected to an external driving force is changed, and the balanced position of the rotary shaft 7 is adjusted, such that the balanced position of the rotary shaft 7 is corrected when the balanced position of the rotary shaft 7 deviates from a target position.

Various embodiments provided by the present invention have the following beneficial effects:

1. in the present embodiment of the present invention, since the connection shaft can move upward under the driving of the drive part, one end of the cap removal member is pivotally connected to the connection shaft, and the cap removal member rotates round the pivot point, when the drive part drives the connection shaft to move upwards, the other end of the cap removal member moves downward around the pivot point to further contact the cap and press the cap till the cap is removed, thereby realizing automatic removal of the cap, and improving the cap removal efficiency and the detection efficiency.

2. In the embodiment of the present invention, since the control unit is configured to control, in response to the cap removal request, the drive part to drive the connection shaft to move upwards, the automatic control of the cap removal device and the automated cap removal process are achieved, the operating efficiency is improved and the problem of difficulty in manual cap removal is solved.

3. In the embodiment of the present invention, since one end of the cap removal member is provided with a through hole, and one end of the cap removal member passes through the through hole, is connected to the pivot shaft of the connection shaft and is pivotally connected to the connection shaft, the dimension of the through hole in the length direction of the cap removal member is larger than the diameter of the pivot shaft, such that when the rotary shaft moves upwards and downwards to drive the cap removal member to rotate around the pivot point, the pivot shaft can slide within the through hole, thereby ensuring the linear movement of the connection shaft in parallel to its axis and simplifying the structure.

4. In the embodiment of the present invention, since the other end of the cap removal mechanism is provided with the opening, and the rotary shaft passes through the opening in a manner of substantially perpendicular to the other end, the other end sleeves the rotary shaft. Since the opening is not in contact with the rotary shaft, the interference with the rotating rotary shaft can be avoided, and meanwhile, the opening plays a certain guide role when the rotary shaft moves downward.

5. In the embodiment of the present invention, the fixed support part supports the movable support part and the supported object by means of the connection part. The first connection part and the second connection part in the connection part are connected together in a form of point contact. The supported object which is in stress drives the movable support part to rotate around the contact point between the first connection part and the second connection part. Since the first connection part and the second connection part are connected together in a form of point contact, when the movable support part and the fixed support part rotate relative to each other, only one contact point generates a frictional force to impede the rotation of the movable support part. Therefore, compared with the prior art in which the frictional force is generated by a plurality of contact points, the frictional force generated on the support may be reduced, and thus the rotational resistance encountered when the supported object rotates is reduced.

6. In the embodiment of the present invention, two connection parts included in the connection part may be the jewel bearing and the top cone. The tip of the top cone is located in the tapered groove of the jewel bearing, and the tip of the top cone is in point contact with the bottom of the tapered groove. When the jewel bearing rotates relative to the top cone, a less frictional force is generated, such that the rotational resistance from the support when the supported object rotates can be reduced. The sensitivity and the measurement accuracy of the thrombelastography device may be improved when the support is applied to the thrombelastography device.

7. In the embodiment of the present invention, the support may comprise at least a pair of magnets, wherein one magnet in each pair of magnets is fixed to the fixed support part, and the other magnet thereof is fixed to the movable support part. The pair of magnets is stacked in parallel, and like magnetic poles are opposite. In this way, according to the principle that like poles repel each other, the magnet on the fixed support part provides an upward magnetic force to the magnet on the movable support part. The magnetic force can reduce the pressure of the point contact between the first connection part and the second connection part, and further reduce the frictional force generated by the point contact, thereby further reducing the rotational resistance encountered when the supported object rotates.

8. In the embodiment of the present invention, the reflective sheet reflects the light emitted by the light emitting module to the light receiving module. When the reflective sheet rotates under the driving of the rotary shaft, since the light emitting module emits light in a fixed direction, the amount of light received by the reflective sheet changes, and at the same time, the optical path of light reflected by the reflective sheet changes due to the rotation of the reflective sheet, resulting in a change in the intensity of light received by the light receiving module that receives the light in the fixed direction. The light receiving module converts the received light into a corresponding electrical signal according to the intensity of the light. The processing module determines the rotation angle of the rotary shaft according to the electrical signal. In this case, the light is taken as a signal for detecting the rotation angle of the rotary shaft. Since the intensity of the light does not change as external factors such as temperature change, the accuracy of detecting the rotation angle of the rotary shaft can be improved by detecting the rotation angle of the rotary shaft through light.

9. In the embodiment of the present invention, the light emitting diode emits light through the light guide column, and the photocell receives light through the light guide column. The light guide column which serves as a light channel can enhance the uniformity of light and prevent the light from being diffusely reflected in the through hole of the fixed light emitting diode or the photocell to affect the intensity of the light, thereby ensuring the detection accuracy of the rotation angle of the rotary shaft.

10. In the embodiment of the present invention, the rotary shaft is able to rotate under the support of the support, and the position correction device is connected to the rotary shaft. When the rotary shaft rotates away from a balanced position under the driving force of the measured blood, the position correction device is caused to generate an acting force for rotating the rotary shaft towards the balanced position. In this way, when the driving effect of the measured blood on the rotary shaft is removed, if the position where the rotary shaft is located is not the balanced position, the rotary shaft automatically returns to the balanced position under the acting force of the position correction device, and thus does not need to be calibrated by manual adjustment. Therefore, the time of calibrating the rotary shaft is saved, and the efficiency in blood coagulation measurement is improved.

11. In the embodiment of the present invention, the position correction device may comprise at least one hair spring, wherein the inner ring of the hair spring is fixedly connected to the rotary shaft, and the outer ring of the hair spring is fixedly connected to the support. When the rotary shaft rotates away from the balanced position, the hair spring deforms. The elastic force generated as the hair spring deforms acts on the rotary shaft. The acting direction of the elastic force is the direction in which the rotary shaft restores to the balanced position. Since the hair spring is light in weight and sensitive in response, the hair spring is used as the position correction device to reduce the inertia of selecting the axis and the resistance received during the rotation, and improve the accuracy of the thrombelastography device. The position correction device may comprise a plurality of hair springs, wherein the spiral direction of a part of hair springs among all of the hair springs is opposite to the spiral direction of the other hair springs, such that a part of hair springs are screwed when the rotary shaft rotates in different directions. By means of such a structure, the service life of the hair springs may be prolonged, and the rotary shaft can rotate stably.

12. In the embodiment of the present invention, the hair springs are fixed to the support by means of the zero setting modules, and the position of the zero setting module, which is connected to the outer ring of the hair spring is adjustable, such that the balanced position of the rotary shaft can be adjusted by adjusting the position of the zero setting module, which is connected to the outer ring of the hair spring. Therefore, the balanced position of the rotary shaft is calibrated to improve the usability of the thrombelastography device.

It should be noted that the terms "processor", "processing unit/module", "controller", "control unit/module" or the like appearing herein may be appropriate devices that are capable of executing appropriate program instructions, arithmetic operations, data processing, and/or control operations and the like. These appropriate devices may be software, hardware, firmware, or a combination thereof, such as, for example, a computer, a central processing unit, or the like. They may be composed of single components or or dispersed over a plurality of components according to their functions. They may be a centralized processing system or a distributed processing system.

ASPECTS OF THE INVENTION

1. A cap removal device, comprising a drive part, a connection shaft, and a cap removal member, wherein
the connection shaft can move upward when driven by the drive part;
the cap removal member has an end and the other end; the end is pivotally connected to the connection shaft, so that when the connection shaft moves upward when driven by the drive part, the cap removal member rotates, due to the upward movement, around a pivot point located between the end and the other end of the cap removal member, so that the other end of the cap removal member moves downward to contact a cap to be removed, thereby removing the cap.

2. The cap removal device according to aspect 1, wherein the end of the cap removal device is provided with a through hole; the connection shaft is provided with a pivot shaft; the end passes through the through hole, and is connected to the pivot shaft of the connection shaft, and pivotally connected to the connection shaft.

3. The cap removal device according to aspect 2, wherein a dimension of the through hole in a length direction of the cap removal member is larger than a diameter of the pivot shaft, such that the pivot shaft is able to slide in the through hole when the connection shaft moves upward and downward to the cap removal member to rotate around the pivot point.

4. The cap removal device according to aspect 3, wherein the drive part drives the connection shaft in a vertical straight line direction.

5. The cap removal device according to aspect 1, further comprising a control unit which is configured to, in response a cap removal request, control the drive part to drive the connection shaft to move upward.

6. The cap removal device according to aspect 1, wherein the cap removal member comprises a first part and a second part which are fixedly connected, wherein the first part comprises the end and the second part comprises the other end.

7. The cap removal device according to aspect 6, wherein the first part and the second part form a certain inclination angle.

8. The cap removal device according to aspect 7, wherein the pivot point is located on the first part.

9. The cap removal device according to any one of claims 1 to 8, wherein the cap is able to sleeve a rotary shaft; the other end is provided with an opening, such that the rotary shaft is able to pass through the opening in a manner substantially perpendicular to the other end, and further the other end sleeves the rotary shaft; in the course of use, the cap sleeves the rotary shaft and is located below the opening.

10. The cap removal device according to aspect 9, wherein the rotary shaft is supported by a support; the drive part is fixed to the support, and the cap removal member is pivotally connected to the support at the pivot point.

11. The cap removal device according to any one of aspects 1 to 8, wherein the drive part is an electromagnet, and at least part of the connection shaft is made of a material that can be attracted by the electromagnet.

12. A thrombelastography device, comprising a support, a rotary shaft and the cap removal device according to any one of aspects 1 to 11, wherein
the support is connected to one end of the rotary shaft to support the rotary shaft, such that the rotary shaft is able to rotate under an external driving force;
the cap removal member is pivotally connected to the support at the pivot point;
the other end of the cap removal member is provided with an opening that allows the rotary shaft to pass through in a manner substantially perpendicular to the other end, such that the other end sleeve the rotary shaft; and
the cap sleeves the rotary shaft and is located below the opening.

13. The thrombelastography device according to aspect 12, wherein the support comprises a fixed support part, a movable support part, a first connection part and a second connection part;
the first connection part is fixedly connected to the fixed support part, and the second connection part is fixedly connected to the movable support part;
the first connection part and the second connection part are connected together in a form of point contact, such that the second connection part is able to rotate relative to the first connection part; and
the movable support part is fixedly connected to one end of the rotary shaft.

14. The thrombelastography device according to aspect 13, wherein the first connection part comprises a jewel bearing, and the second connection part comprises a top cone;
or
the first connection part comprises a top cone, and the second connection part comprises a jewel bearing; wherein the jewel bearing is provided with a tapered groove, the top cone is of a tapered structure, the tip of the top cone is located in the tapered groove in the jewel bearing, and the top cone is connected to the jewel bearing in a form of point contact.

15. The thrombelastography device according to aspect 13, wherein the support further comprises at least a pair of magnets;

for each pair of magnets, the first magnet is fixed to one side, close to the movable support part, on the fixed support part, and the second magnet is fixed to one side, close to the fixed support part, on the movable support part; and the first magnet and the second magnet are stacked in parallel, and two surfaces that are close each other have like magnetic poles.

16. The thrombelastography device according to any one of aspects 12 to 15, further comprising a measurement device which is used for measuring a rotation angle of the rotary shaft, and forming a thrombelastogram corresponding to measured blood according to the rotation angle of the rotary shaft.

17. The thrombelastography device according to aspect 16, wherein the measurement device comprises at least one reflective sheet, at least one light emitting module, at least one light receiving module and a processing module;

the rotary shaft is fixedly connected to the at least one reflective sheet and drives the at least one reflective sheet to rotate under an external driving force;

each of the light emitting modules is used for emitting light to the corresponding reflective sheet in a fixed direction;

each of the reflective sheets is used for receiving light emitted by the corresponding light emitting module and reflecting the received light;

each of the light receiving modules is used for receiving light reflected by a corresponding reflective sheet in a fixed direction, converting the received light into a corresponding electrical signal according to the intensity of the light, and transmitting the electrical signal to the processing module; and the processing module is used for processing the electrical signal converted by the at least one light receiving module to determine the rotation angle of the rotary shaft.

18. The thrombelastography device according to aspect 17, wherein the light emitting module comprises a light emitting diode and a light guide column, wherein the light emitting diode emits light to the reflective sheet through the light guide column;

and/or the light receiving module comprises a photocell and a light guide column, wherein the photocell receives light reflected by the reflective sheet through the light guide column.

19. The thrombelastography device according to aspect 12, further comprising a position correction device, wherein the other end of the rotary shaft is placed in measured blood, and the rotary shaft is able rotate under the driving force of the measured blood; and the position correction device is connected to the rotary shaft and is used for generating, when the rotary shaft rotates away from a balanced position, an acting force that rotates the rotary shaft back to the balanced position.

20. The thrombelastography device according to aspect 19, wherein the position correction device comprises at least one hair spring, wherein an inner ring of each of the hair springs is fixedly connected to an outer circumferential surface of the rotary shaft, and an outer ring of each of the hair springs is fixedly connected to the support.

21. The thrombelastography device according to aspect 21, wherein the at least one hair spring is two or more hair springs, and the spiral direction of at least one hair springs in the two or more hair springs from the inner ring to the outer ring is opposite to the spiral direction of the other hair spring from the inner ring to the outer ring.

22. The thrombelastography device according to aspect 20, wherein the position correction device further comprises at least one zero setting module, wherein each zero setting module corresponds to one of the hair springs; one end of each zero setting module is fixedly connected to the support, and the other end of the zero setting module is fixedly connected to different positions on the outer ring of the corresponding hair spring in an adjustable manner, thereby adjusting the balanced position.

The above description is only specific embodiments of the present invention, but the protection scope of the present invention is not limited thereto. Any variations or substitutions of the present invention, which are easily conceived by those skilled in the art in the technical scope of the present invention, should be included in the protection scope of the present invention. Therefore, the protection scope of the present invention should be subject to the protection scope of the claims.

The invention claimed is:

1. A thrombelastography device, comprising a support, a rotary shaft and a cap removal device, wherein the support is connected to one end of the rotary shaft to support the rotary shaft, such that the rotary shaft is able to rotate, wherein the rotary shaft is able to be sleeved with the cap to be removed;

the cap removal device comprises a drive part, a connection shaft, and a cap removal member, wherein the connection shaft can move upward when driven by the drive part;

the cap removal member has a first end and a second end; the first end is pivotally connected to the connection shaft, so that when the connection shaft moves upward when driven by the drive part, the cap removal member rotates, due to the upward movement, around a pivot point located between the first end and the second end of the cap removal member, so that the second end of the cap removal member moves downward to contact the cap to be removed, thereby removing the cap;

the cap removal member is pivotally connected to the support at the pivot point; and the second end of the cap removal member is provided with an opening that allows the rotary shaft to pass through in a manner substantially perpendicular to the second end, such that the second end sleeves the rotary shaft and is located above the cap, and wherein the first end of the cap removal member has a through hole; the connection shaft has a pivot shaft; the cap removal member is pivotally connected to the connection shaft at the first end by engaging the through hole of the cap removal member with the pivot shaft of the connection shaft.

2. The thrombelastography device according to claim 1, wherein a dimension of the through hole in a length direction of the cap removal member is larger than a diameter of the pivot shaft, such that the pivot shaft is able to slide in the through hole when the connection shaft moves upward and downward to drive the cap removal member to rotate around the pivot point.

3. The thrombelastography device according to claim 1, wherein the cap removal device further comprises a control unit which is configured to, in response a cap removal request, control the drive part to drive the connection shaft to move upward.

4. The thrombelastography device according to claim 1, further comprising a measurement device which is used for measuring a rotation angle of the rotary shaft, and forming a thrombelastogram corresponding to measured blood according to the rotation angle of the rotary shaft.

5. The thrombelastography device according to claim 4, wherein
the measurement device comprises at least one reflective sheet, at least one light emitting module, at least one light receiving module and a processing module;
the rotary shaft is fixedly connected to the at least one reflective sheet and drives the at least one reflective sheet to rotate under an external driving force;
each of the light emitting modules is used for emitting light to the corresponding reflective sheet in a fixed direction;
each of the reflective sheets is used for receiving light emitted by the corresponding light emitting module and reflecting the received light;
each of the light receiving modules is used for receiving light reflected by a corresponding reflective sheet in a fixed direction, converting the received light into a corresponding electrical signal according to the intensity of the light, and transmitting the electrical signal to the processing module; and
the processing module is used for processing the electrical signal converted by the at least one light receiving module to determine the rotation angle of the rotary shaft.

6. The thrombelastography device according to claim 5, wherein
the light emitting module comprises a light emitting diode and a light guide column, wherein the light emitting diode emits light to the reflective sheet through the light guide column;
and/or
the light receiving module comprises a photocell and a light guide column, wherein the photocell receives light reflected by the reflective sheet through the light guide column.

7. A thrombelastography device, comprising a support, a rotary shaft and a cap removal device, wherein
the support is connected to one end of the rotary shaft to support the rotary shaft, such that the rotary shaft is able to rotate, wherein the rotary shaft is able to be sleeved with the cap to be removed;
the cap removal device comprises a drive part, a connection shaft, and a cap removal member, wherein
the connection shaft can move upward when driven by the drive part;
the cap removal member has a first end and a second end an end and the other end; the first end is pivotally connected to the connection shaft, so that when the connection shaft moves upward when driven by the drive part, the cap removal member rotates, due to the upward movement, around a pivot point located between the first end and the second end of the cap removal member, so that the second end of the cap removal member moves downward to contact the cap to be removed, thereby removing the cap;
the cap removal member is pivotally connected to the support at the pivot point; and
the second end of the cap removal member is provided with an opening that allows the rotary shaft to pass through in a manner substantially perpendicular to the second end, such that the second end sleeves the rotary shaft and is located above the cap, and
wherein the cap removal member comprises a first part and a second part which are fixedly connected, wherein the first part comprises the first end of the cap removal member and the second part comprises the second end of the cap removal member, and the first part and the second part form a certain inclination angle.

8. A thrombelastography device, comprising a support, a rotary shaft and a cap removal device, wherein
the support is connected to one end of the rotary shaft to support the rotary shaft, such that the rotary shaft is able to rotate, wherein the rotary shaft is able to be sleeved with the cap to be removed;
the cap removal device comprises a drive part, a connection shaft, and a cap removal member, wherein
the connection shaft can move upward when driven by the drive part;
the cap removal member has a first end and a second end; the first end is pivotally connected to the connection shaft, so that when the connection shaft moves upward when driven by the drive part, the cap removal member rotates, due to the upward movement, around a pivot point located between the first end and the second end of the cap removal member, so that the second end of the cap removal member moves downward to contact the cap to be removed, thereby removing the cap;
the cap removal member is pivotally connected to the support at the pivot point; and
the second end of the cap removal member is provided with an opening that allows the rotary shaft to pass through in a manner substantially perpendicular to the second end, such that the second end sleeves the rotary shaft and is located above the cap, and
wherein
the support comprises a fixed support part, a movable support part, a first connection part and a second connection part;
the first connection part is fixedly connected to the fixed support part, and the second connection part is fixedly connected to the movable support part;
the first connection part and the second connection part are connected together in a form of point contact, such that the second connection part is able to rotate relative to the first connection part; and
the movable support part is fixedly connected to one end of the rotary shaft.

9. The thrombelastography device according to claim 8, wherein
the first connection part comprises a jewel bearing, and the second connection part comprises a top cone;
or
the first connection part comprises a top cone, and the second connection part comprises a jewel bearing;
wherein
the jewel bearing is provided with a tapered groove, the top cone is of a tapered structure, the tip of the top cone is located in the tapered groove in the jewel bearing, and the top cone is connected to the jewel bearing in a form of point contact.

10. The thrombelastography device according to claim 8, wherein
the support further comprises at least a pair of magnets;

for each pair of magnets, the first magnet is fixed to one side, close to the movable support part, on the fixed support part, and the second magnet is fixed to one side, close to the fixed support part, on the movable support part; and the first magnet and the second magnet are stacked in parallel, and two surfaces that are close each other have like magnetic poles.

11. The thrombelastography device according to claim 10, further comprising a position correction device, wherein an other end of the rotary shaft is placed in measured blood, and the rotary shaft is able rotate under a driving force of the measured blood; and the position correction device is connected to the rotary shaft and is used for generating, when the rotary shaft rotates away from a balanced position, an acting force that rotates the rotary shaft back to the balanced position, wherein the position correction device comprises at least one hair spring, wherein an inner ring of each of the hair springs is fixedly connected to an outer circumferential surface of the rotary shaft, and an outer ring of each of the hair springs is fixedly connected to the support.

12. The thrombelastography device according to claim 11, wherein the at least one hair spring is two or more hair springs, and the spiral direction of at least one hair springs in the two or more hair springs from the inner ring to the outer ring is opposite to the spiral direction of the other hair spring from the inner ring to the outer ring.

13. The thrombelastography device according to claim 11, wherein the position correction device further comprises at least one zero setting module, wherein each zero setting module corresponds to one of the hair springs; one end of each zero setting module is fixedly connected to the support, and an other end of the zero setting module is fixedly connected to different positions on the outer ring of the corresponding hair spring in an adjustable manner, thereby adjusting the balanced position.

* * * * *